(12) United States Patent
Gallamini

(10) Patent No.: US 11,278,735 B2
(45) Date of Patent: Mar. 22, 2022

(54) LASER-THERAPY DEVICE

(71) Applicant: FREMSLIFE S.r.l., Genoa (IT)

(72) Inventor: Michele Gallamini, Genoa (IT)

(73) Assignee: FREMSLIFE S.r.l., Genoa (IT)

( * ) Notice: Subject to any disclaimer, the term of this patent is extended or adjusted under 35 U.S.C. 154(b) by 5 days.

(21) Appl. No.: 16/611,448

(22) PCT Filed: May 10, 2017

(86) PCT No.: PCT/IB2017/052721
§ 371 (c)(1),
(2) Date: Nov. 6, 2019

(87) PCT Pub. No.: WO2018/207000
PCT Pub. Date: Nov. 15, 2018

(65) Prior Publication Data
US 2020/0206528 A1 Jul. 2, 2020

(51) Int. Cl.
*A61N 5/067* (2006.01)
*A61N 5/06* (2006.01)

(52) U.S. Cl.
CPC ............ *A61N 5/0619* (2013.01); *A61N 5/067* (2021.08); *A61N 2005/0628* (2013.01)

(58) Field of Classification Search
None
See application file for complete search history.

(56) References Cited

U.S. PATENT DOCUMENTS

| 5,024,236 A | 6/1991 | Shapiro |
| 6,975,908 B1 * | 12/2005 | Nødskov ............ A61H 39/002 607/145 |

(Continued)

FOREIGN PATENT DOCUMENTS

| CN | 1077110 A | * | 10/1993 |
| CN | 1115681 A | * | 1/1996 |

(Continued)

OTHER PUBLICATIONS

Patent Cooperation Treaty, International Search Report and Written Opinion for International Application No. PCT/IB2017/052721, 10 pages, dated Sep. 2, 2018.

*Primary Examiner* — Michael W Kahelin
*Assistant Examiner* — Michael A Rizzuto
(74) *Attorney, Agent, or Firm* — Stetina Brunda Garred and Brucker

(57) ABSTRACT

An improved laser-therapy device for the treatment of acupuncture points, which comprises:
 a control unit;
 laser emitting means associated to said control unit;
 means for generating an emission signal, which are functionally associated to said control unit and to said laser emitting means; and
 means for modulating said emission signal, which are designed to generate a modulated signal,
 wherein said modulated signal derives from a first square-wave modulation at a frequency of 100 Hz combined with a second square-wave modulation at a frequency of between 1 and 2 Hz,
 characterized in that a third square-wave modulation at a frequency of between 50 and 200 Hz is provided, combined, respectively, with said first and second modulations,
 characterized in that a third square-wave modulation at a frequency of between 5 and 20 Hz is provided, combined, respectively, with said first and second modulations.

8 Claims, 3 Drawing Sheets

(56) References Cited

U.S. PATENT DOCUMENTS

| | | | |
|---|---|---|---|
| 2005/0203592 A1* | 9/2005 | Teichert | A61N 5/0622 607/88 |
| 2012/0053648 A1* | 3/2012 | Neher | A61H 39/002 607/3 |
| 2012/0089206 A1* | 4/2012 | Wu | A61N 5/0618 607/89 |
| 2015/0057648 A1* | 2/2015 | Swift | A61B 18/245 606/15 |

FOREIGN PATENT DOCUMENTS

| | | | | |
|---|---|---|---|---|
| CN | 105561482 | | 5/2016 | |
| EP | 1669102 | | 6/2006 | |
| EP | 1669102 | A1 * | 6/2006 | A61N 5/0619 |
| WO | WO-2006049570 | A2 * | 5/2006 | A61N 5/0619 |

\* cited by examiner

LASER-THERAPY DEVICE

CROSS-REFERENCE TO RELATED APPLICATIONS

The present application claims priority to PCT International Application No. PCT/IB2017/052721 filed on May 10, 2017, the entirety of the disclosure of which is expressly incorporated herein by reference.

STATEMENT RE: FEDERALLY SPONSORED RESEARCH/DEVELOPMENT

Not applicable

DESCRIPTION

Field of the Invention

The present invention relates to an improved laser-therapy device used in particular but not exclusively for transmitting opto-electromagnetic energy to points of the body surface, that are energetically active, with values of electrical conductivity lower than those of the surrounding tissues and characterized by a considerably higher concentration of nerve receptors, said points being referred to as "acupuncture points".

Brief Remarks on the Prior Art

Laser-therapy apparatuses are known that are able to emit light radiation, mainly laser radiation, for the treatment of both acute and chronic pathological conditions. In particular, laser-therapy treatments are conducted in the case where it is necessary to increase the rate of recovery in the repair of damaged tissues, provide relief in the case of painful syndromes, or else reduce inflammation.

Improvement of such apparatuses has been concentrated on the effectiveness of stimulating physiological responses through signals conveyed to the body of the patient at different energies. An example of laser-therapy apparatus is described in the document No. EP1669102. This apparatus is configured for supplying a low-energy stimulation, which is able to interact with the biological system, imitating the "biological signal" produced by the metabolism of healthy tissues.

SUMMARY OF THE INVENTION

Object of the present invention is consequently to provide an improved laser-therapy device that will enhance the performance and efficiency of the systems according to the prior art.

Yet a further object of the present invention is to provide an improved laser-therapy device that will be constructionally simple and economical to produce.

These and other objects are achieved by an improved laser-therapy device for the treatment of an acupuncture point, which comprises:
  a control unit;
  laser emitting means associated to said control unit;
  means for generating an emission signal, which are functionally associated to said control unit and to said laser emitting means; and
  means for modulating said emission signal, which are designed to generate a modulated signal,
  wherein said modulated signal derives from a first square-wave modulation at a frequency of 100 Hz combined with a second square-wave modulation at a frequency of between 1 and 2 Hz,
  characterized in that a third square-wave modulation at a frequency of between 5 and 20 Hz is provided, which is combined, respectively, with said first and second modulations;
  in which a third square-wave modulation at a frequency of between 5 and 20 Hz is provided, which is combined, respectively, with said first and second modulations;
  Advantageously, said first, second, and third modulations are emitted in combination through a logic sum (AND) starting from the highest frequency in such a way that the resulting emission will be a time-modulated sequence of pulse trains at the basic frequency (see the drawing).

More in particular, the first modulation or carrier modulation at 100 Hz is designed to interact with the metabolism of the proteoglycans of the extra-cellular matrix (ECM).

The second modulation at 1-2 Hz, in addition to preventing phenomena of habituation to the stimulation at 100 Hz, favours, precisely on account of the pulsation of said emission, the differentiated synthesis of endogenous opioids and the stimulation of various nerve fibres.

Finally, the third modulation has the purpose of favouring the diffusion of the stimulus along the acupuncture meridian of which a particular point has been stimulated. Transmission of the signal of stimulation induced on the meridian occurs in fact through mechanical modulations that can benefit from the specific oscillatory resonance frequencies that are proper to each meridian.

Advantageously, these modulation means enable regulation of the average power delivered by said laser emitting means through the modulation of duty-cycle parameter, maintaining the parameters of frequency and peak power that are defined in relation to the physiological functions. In this way, since the power is obtained by multiplying the peak power by the product of the duty cycles of the various modulations, by setting a specific value of mean power (lower than the rated power), the device modifies in the same ratio the duty cycle of each of the modulations envisaged.

Preferably, a point-targeting module of an impedentiometric type is provided, designed to locate the acupuncture point to be treated.

In particular, the point-targeting module comprises:
  a rod provided with a contact head, wherein said rod is slidably mounted in a case, by means of a first spring and a second spring opposed to one another;
  a slider provided on said rod in a median position, wherein said slider slides in a channel provided on the cylindrical body, with a position indicator, in such a way that, when the contact head is set resting in operation on the skin of the patient, the slider shifts from a neutral position to a measuring position to indicate a predetermined pressure value;
  an a.c. generator for generating alternating current, which is made to flow in the body of the patient to enable measurement of the impedance; this generator is connected to the contact head, which is made to slide in the proximity of the acupuncture target point and, through a contact clamp of a commercially available type, to some other part of the body.

Advantageously, provided on the end of the rod opposite to the contact head is a conductor, functionally connected to a measuring instrument.

Advantageously, the signal detected will be demodulated through a diode bridge, and the d.c. voltage at output, through a suitable amplifier with high input insulation, will be connected to the indicator modules.

In a preferred embodiment, a sensing unit for detecting the optical power effectively delivered is provided. This sensing unit comprises an array of phototransistors accommodated in a cylindrical cavity, housed within which is the light-emitting diode. The laser beam is oriented towards the bottom of said cavity, which is advantageously provided with a concave reflector on the bottom and painted opaque black so as not to generate any further reflections. The array of sensors, appropriately inclined towards the bottom of the cavity, will supply a signal proportional to the optical power measured. Through a purposely designed circuitry the signal will be digitized and transferred to the processing and control module.

BRIEF DESCRIPTION OF THE DRAWINGS

Further characteristics and/or advantages of the present invention will appear more clearly from the following description of a number of embodiments, which are provided by way of non-limiting example, with reference to the annexed drawings, in which.

DESCRIPTION OF PREFERRED EMBODIMENTS

Figure 1:
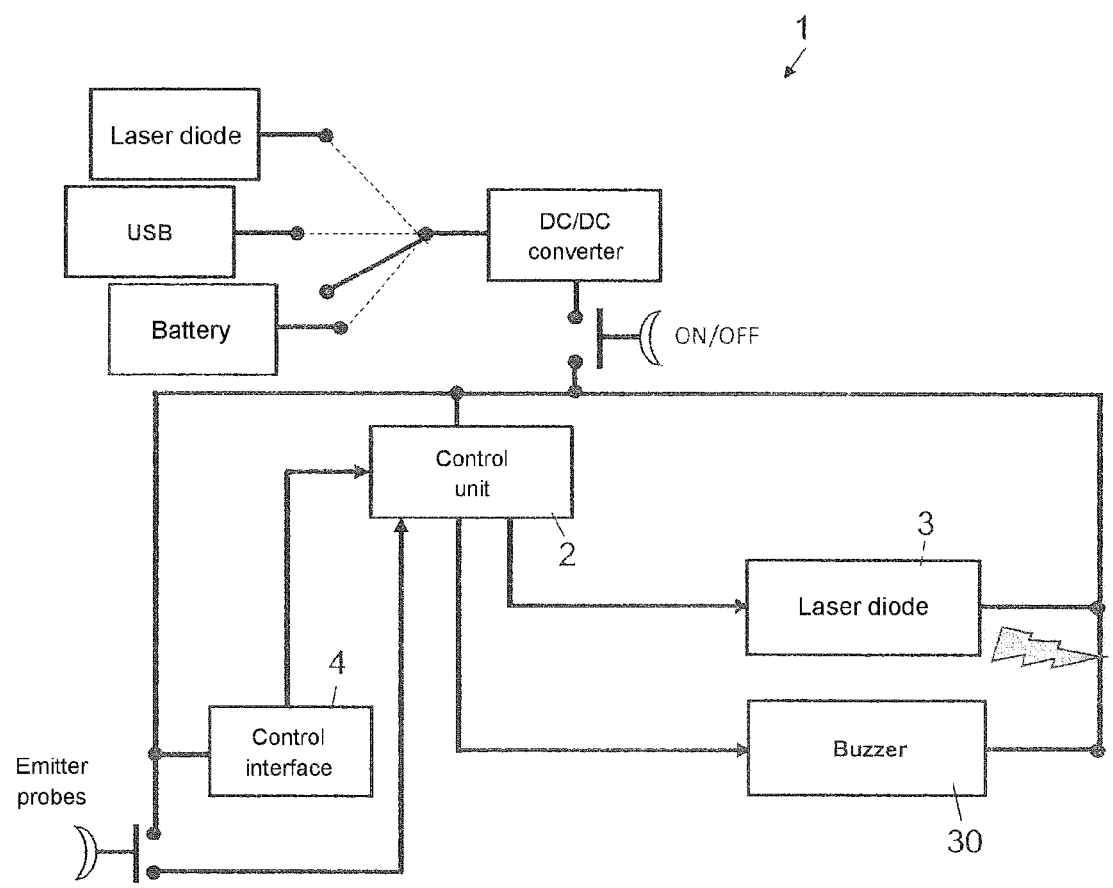
FIG. 1 is a block diagram of an improved laser-therapy device according to the present invention.

With reference to FIG. 1, illustrated therein is an improved laser-therapy device 1 that comprises a control unit 2, for example a processor CPU and laser emitting means 3, for example a laser diode, functionally connected and controlled by the control unit 2. Furthermore, the device 1 comprises means, or interface unit (or control interface) 4, for generating an emission signal, which are also functionally associated to the control unit 2 and to the laser 3, and a modulation module 5 for modulating the emission signal designed to generate a modulated signal. In particular, the modulated signal derives from a first square-wave modulation at a frequency of 100 Hz combined with a second square-wave modulation at a frequency of between 1 and 2 Hz. Furthermore, a third square-wave modulation at a frequency of between 5 and 20 Hz is provided, combined, respectively, with said first and second modulations.

The first, second, and third modulations are added starting from the highest frequency in a way that the resulting emission will be a time-modulated sequence of pulse trains at the basic frequency. This solution responds to the need for selective and combined stimulation of different physiological mechanisms, limiting the dosimetry of energy of irradiation on the specific acupuncture point to around 0.1 mJ.

More in particular, the first modulation or carrier modulation at 100 Hz is designed to interact with the metabolism of the proteoglycans of the extra-cellular matrix (ECM). For instance, in "normal" conditions of homeostasis in healthy subjects at the body temperature of around 37° C., the proteoglycans follow a cycle of oxidation-reduction with a period of between 6 and 20 ms corresponding to the frequencies of 160 and 50 Hz, respectively. During these activities of oxidation and reduction there enter into play the emissions/absorptions of photons, which, at the temperature of 37° C., have the wavelength of around 650 nm. The carrier modulation hence has the purpose of "mimicking" and integrating the metabolic activities, suggesting a "normal" condition. It in turn maintains a pH and physical characteristics of the ECM in conditions such as to allow regular intercellular exchange. The supplement of stimulation has proven able to favour the metabolism of endogenous opioids at a spinal level and of the upper motor neuron, with consequent analgetic effects.

The second modulation at 1-2 Hz, in addition to preventing phenomena of habituation to the stimulation at 100 Hz, favours, precisely on account of the pulsation of said emission, the synthesis of different endogenous opioids and the stimulation of various nerve fibres.

Finally, the third modulation has the purpose of favouring diffusion of the stimulus along the acupuncture meridian of which a particular point has been stimulated. Transmission of the signal of stimulation induced on the meridian occurs in fact through mechanical modulations that can benefit from the specific oscillatory resonance frequencies that are proper to each meridian.

Furthermore, the control unit 2 is configured for regulating the mean power delivered by the laser 3, maintaining the parameters of frequency and peak power that are defined in relation to the physiological functions. In this way, since the power is obtained by multiplying the peak power by the product of the duty cycles of the various modulations, by setting a specific value of mean power (lower than the rated power), the device 1 modifies in the same ratio the duty cycle of each of the modulations envisaged.

Figure 2:
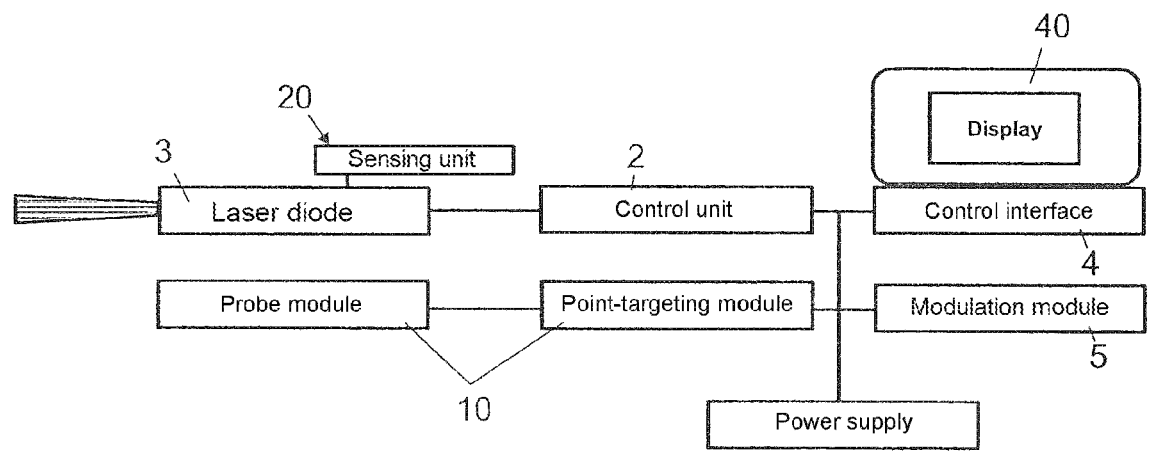
FIG. 2 is a schematic view of the device of FIG. 1.

In other words, the control unit 2 verifies the emission of the modulated control square wave for the laser diode 3 according to the settings. By means of the control interface 4, it carries out calculation of the energy effectively emitted on the basis of the settings, via time integration of the mean power of the emission itself. The corresponding value is represented on the display 40 of the control interface 4 (FIG. 2). Moreover appearing on the display are all the operations and the parameters (selected mode, frequencies, values of the duty cycles, and value of the mean radiating power). In addition, it generates an acoustic command, issued through the buzzer 30 (FIG. 1) at the end of the radiation programmed.

Figure 4:
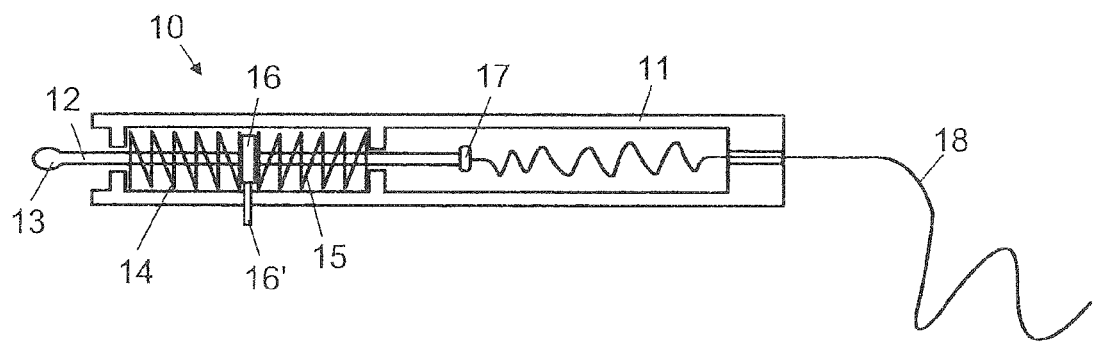
FIG. 4 is a schematic cross-sectional view of a module for locating acupuncture points.
Figure 5:
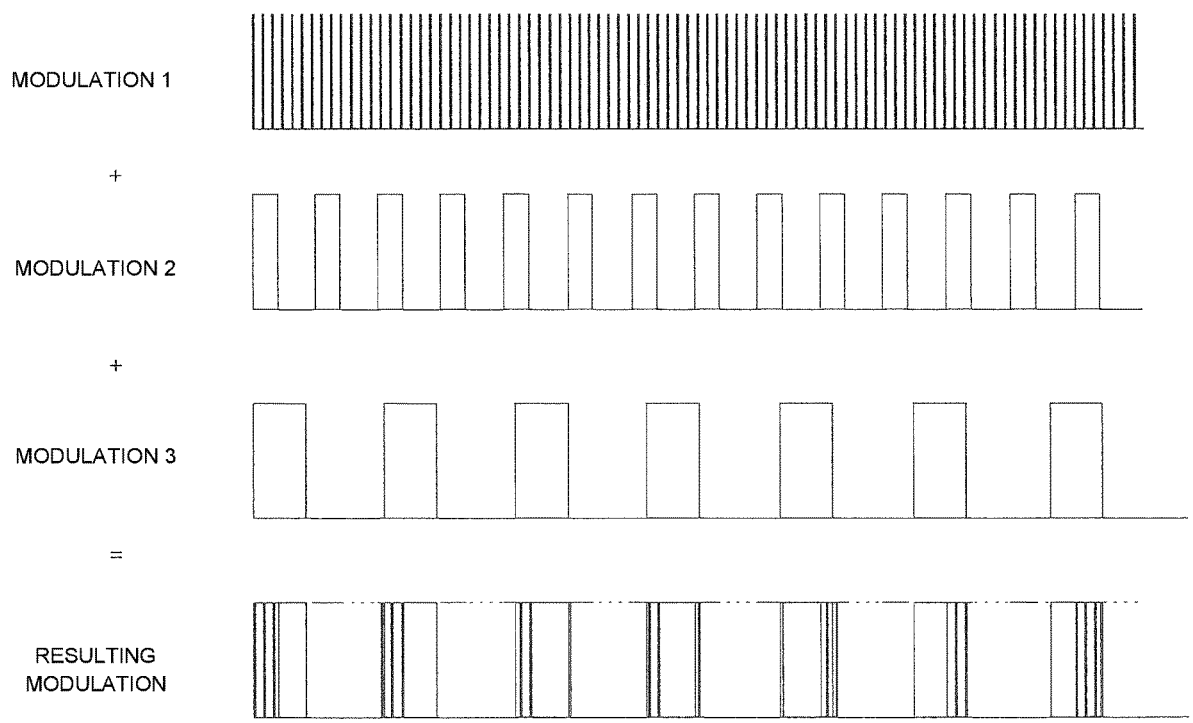
FIG. 5 represents schematically the combination via logic sum of the three modulations envisaged.

With reference to FIG. 2, the device further comprises a point-targeting module 10 of an impedentiometric type, designed to locate the optimal acupuncture point. From a constructional standpoint, as illustrated more clearly in FIG. 4, the point-targeting module 10 comprises a rod 12 provided with a contact head 13. The rod 12 is slidably mounted in a case 11, by means of a first spring 14 and a second spring 15 opposed to one another. In this way, it is possible to maintain a constant pressure on the tissue of the patient.

The excursion of the central point of the rod 12 on which the two springs 14, 15 are applied has a slider 16, which slides in a purposely designed channel provided on the cylindrical body, with a position indicator 16' that indicates the position of the centre of the rod 12 itself. When, during operation, the contact head 13 is set resting on the skin of the patient, it will shift from the neutral position to indicate a predetermined pressure value. Soldered on the inner termination of the rod 12 is a conductor 17 connected by means of a cable 18 to the demodulation and measurement circuit of a measuring instrument (not illustrated). The circuit is closed through the patient by means of a contact clamp (not illustrated either), similar to the one commonly used in ECG. The module is supplied in alternating current at 50 kHz and with a voltage of less than 2 Vpp.

The signal will be demodulated, as illustrated in FIG. 1, through a diode bridge, and the output d.c. voltage, through an appropriate amplifier with high input insulation, will be connected to the indicator modules (a buzzer supplied through the device 1, a VCO Voltage-Controlled Oscillator, and a digital-to-analog converter for driving a purposely provided optical display).

Figure 3:
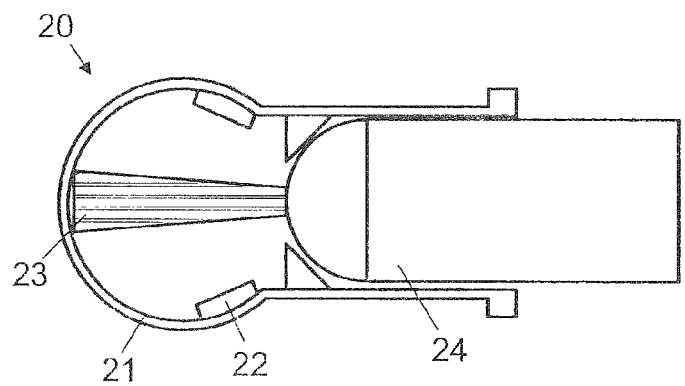
FIG. 3 is a schematic view of the optical-power regulation unit.

In a preferred embodiment, as illustrated in FIG. 3, an optical-power regulation unit is provided comprising a sensing unit 20 for detecting the optical power effectively delivered. This sensing unit 20 comprises an array of phototransistors 22 accommodated within a cylindrical measurement cavity 21, housed within which is the light-emitting diode 24. The emission beam 23 will thus be oriented towards the bottom of the cylindrical measurement cavity 21 provided on the bottom with a concave reflector and painted opaque black so as not to generate any further reflections. The array of sensors 22, appropriately inclined towards the bottom of the cavity, will supply a signal proportional to the optical power measured. Through a purposely designed circuitry, the signal will be digitized and transferred to the processing and control module.

The foregoing description of a number of specific embodiments illustrates the invention from the conceptual standpoint so that others, using the prior art, will be able to modify and/or adapt the specific embodiments in various applications, without the need for any further research and without departing from the inventive idea, and hence it is understood that these adaptations and modifications may be considered as technical equivalents. The means and the materials for implementing the various functions may be of various nature, without thereby departing from the scope of the invention. It is understood that the expressions or terminology used have a purely descriptive and hence non-limiting purpose.

The invention claimed is:

1. An improved laser-therapy device for the treatment of acupuncture points, which comprises:
    a control unit;
    laser emitting means associated to said control unit;
    means for generating an emission signal, which are functionally associated to said control unit and to said laser emitting means; and
    means for modulating said emission signal, which are designed to generate a modulated signal,
    wherein said modulated signal derives from a first square-wave modulation at a frequency of 100 Hz combined with a second square-wave modulation at a frequency of between 1 and 2 Hz,
    characterized in that a third square-wave modulation at a frequency of between 5 and 20 Hz is provided, combined, respectively, with said first and second modulations,
    wherein said first, second, and third modulations are emitted in combination through a logic sum (AND) in such a way that a resulting emission is a time-modulated sequence of pulse trains at the frequency of the first square-wave modulation;
    further comprising a point-targeting module of an impedentiometric type, designed to locate the acupuncture point to be treated;
    wherein said point-targeting module comprises:
    a rod provided with a contact head, wherein said rod is slidably mounted in a case, by means of a first spring and a second spring opposed to one another; and
    a slider provided on said rod in a median position,
    wherein said slider slides in a channel provided on the case, with a position indicator, in such a way that, when the contact head is set resting in operation on the skin of the patient, the slider shifts from a neutral position to a measuring position to indicate a predetermined value of pressure that generates a corresponding measurement signal;
    further comprising a sensing unit for detecting an optical power effectively delivered by said laser, said sensing unit comprising:
    an array of sensors accommodated within a cylindrical cavity, housed within which is the laser emitting means, wherein an emission beam generated is oriented towards a bottom of said cylindrical cavity, and wherein said array of sensors, appropriately inclined towards the bottom of the cavity, are designed to supply a detection signal proportional to the optical power measured, said detection signal being subsequently processed by said control unit.

2. The improved device according to claim 1, wherein said modulation means enable regulation of a mean power delivered by said laser emitting means, maintaining parameters of frequency and peak power that are defined in relation to physiological functions.

3. The improved device according to claim 1, wherein said array of sensors comprises phototransistors.

4. The improved device according to claim 1, wherein said cylindrical cavity is provided with a reflector, which is concave.

5. An improved laser-therapy device for the treatment of acupuncture points, which comprises:
    a control unit;
    laser emitting means associated to said control unit;
    means for generating an emission signal, which are functionally associated to said control unit and to said laser emitting means; and
    means for modulating said emission signal, which are designed to generate a modulated signal,
    wherein said modulated signal derives from a first square-wave modulation at a frequency of 100 Hz combined with a second square-wave modulation at a frequency of between 1 and 2 Hz,
    characterized in that a third square-wave modulation at a frequency of between 50 and 200 Hz is provided, combined, respectively, with said first and second modulations,
    wherein said first, second, and third modulations are emitted in combination through a logic sum (AND) in such a way that a resulting emission is a time-modulated sequence of pulse trains at the frequency of the first square-wave modulation;
    further comprising a point-targeting module of an impedentiometric type, designed to locate the acupuncture point to be treated;
    wherein said point-targeting module comprises:
    a rod provided with a contact head, wherein said rod is slidably mounted in a case, by means of a first spring and a second spring opposed to one another; and
    a slider provided on said rod in a median position,
    wherein said slider slides in a channel provided on the case, with a position indicator, in such a way that, when the contact head is set resting in operation on the skin of the patient, the slider shifts from a neutral position to a measuring position to indicate a predetermined value of pressure that generates a corresponding measurement signal;

further comprising a sensing unit for detecting an optical power effectively delivered by said laser, said sensing unit comprising:

an array of sensors accommodated within a cylindrical cavity, housed within which is the laser emitting means, wherein an emission beam generated is oriented towards a bottom of said cylindrical cavity, and wherein said array of sensors, appropriately inclined towards the bottom of the cavity, are designed to supply a detection signal proportional to the optical power measured, said detection signal being subsequently processed by said control unit.

6. The improved device according to claim 5, wherein said modulation means enable regulation of a mean power delivered by said laser emitting means, maintaining parameters of frequency and peak power that are defined in relation to physiological functions.

7. The improved device according to claim 5, wherein said array of sensors comprises phototransistors.

8. The improved device according to claim 5, wherein said cylindrical cavity is provided with a reflector, which is concave.

* * * * *